United States Patent [19]
Dizon

[11] Patent Number: 5,026,351
[45] Date of Patent: Jun. 25, 1991

[54] IV STYLET CATHETER

[76] Inventor: Cipriano L. Dizon, 161 Springhead Gardens, Richmond Hill, Ontario, Canada

[21] Appl. No.: 484,944

[22] Filed: Feb. 26, 1990

[51] Int. Cl.$^5$ .............................................. A61M 5/178
[52] U.S. Cl. ...................................... 604/164; 604/168; 604/264
[58] Field of Search .............................. 604/164–170, 604/220, 223, 159, 158, 900, 264, 93, 95, 156

[56] References Cited

U.S. PATENT DOCUMENTS

| | | | |
|---|---|---|---|
| 4,108,175 | 8/1978 | Orton | 604/168 |
| 4,191,186 | 3/1980 | Keeler | 604/164 |
| 4,231,367 | 11/1980 | Rash | 604/165 |
| 4,389,208 | 6/1983 | LeVeen et al. | 604/95 |
| 4,631,059 | 12/1986 | Wolvek et al. | 604/280 |
| 4,713,057 | 12/1987 | Huttner et al. | 604/264 |
| 4,752,292 | 6/1988 | Lopez et al. | 604/283 |
| 4,850,961 | 7/1979 | Wanderer et al. | 604/164 |
| 4,911,694 | 3/1990 | Dolan | 604/164 |
| 4,917,669 | 4/1990 | Bonaldo | 604/164 |

Primary Examiner—C. Fred Rosenbaum
Assistant Examiner—Kathleen A. Daley
Attorney, Agent, or Firm—Arne I. Fors

[57] ABSTRACT

An apparatus for the easy subcutaneous insertion of a catheter into a patient is described which includes a main body member having a lockflow chamber, a stylet mounted forwardly of the body member a chamber guard releasably mounted rearwardly of the backflow chamber and a catheter with accompanying live adaptor axially mounted on the stylet with its shaft terminating short of the stylet point. The chamber guard includes a threader member which extends forwardly in a loop to abut the live adapter of the catheter whereby downward pressure on the loop directs the threader member fowward to axially displace the catheter and extend the shaft portion of the catheter beyond the stylet point.

4 Claims, 3 Drawing Sheets

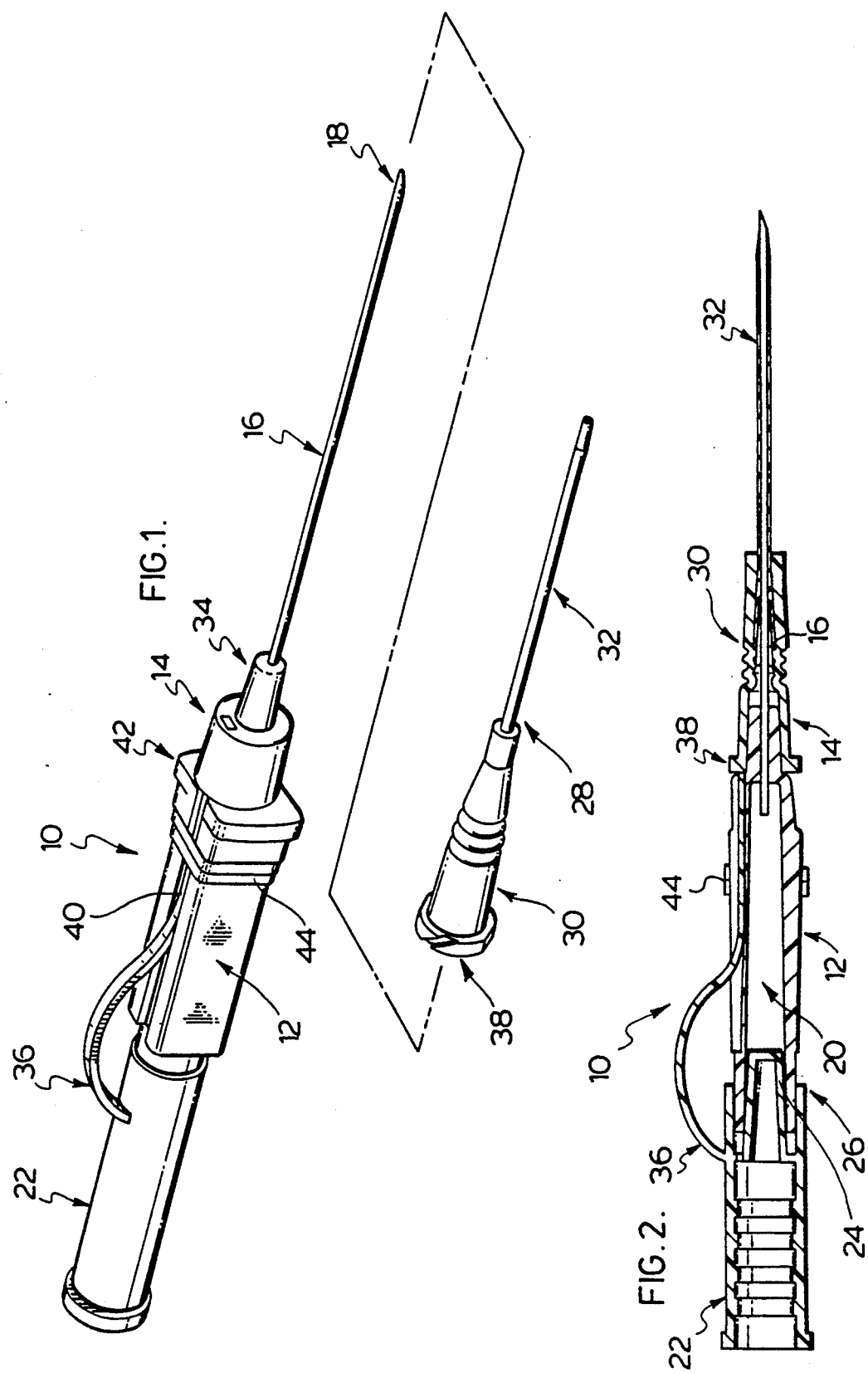

IV STYLET CATHETER

This invention relates to a catheter insertion apparatus having a finger releasing means for directing the catheter forward beyond the stylet point. More particularly, it relates to a catheter insertion apparatus having a single threader member for directing the catheter forward beyond the stylet point into a vein or artery for intravenous or intra arterial application in a patient.

Inserting a catheter into a vein of a patient can sometimes cause trauma due to the accidental puncturing of the vein or due to the slow cumbersome movement by the technician. This is particularly true if the patient is moving or is already under stress.

In normal operations, a catheter apparatus comprising a hollow catheter stylet is secured to a handle portion or body member with the catheter member mounted on the stylet so that its adapter abuts a hub on the body portion. The catheter shaft encases the stylet down to a zone just short of its insertion point. The stylet is then inserted into a vein, drawing a small quantity of blood into the backflow chamber of the handle or body member. This back flow of blood is known as "flashback".

In the catheter insertion apparatus commonly used in the art, the technician then slides the catheter forward by grasping the adapter portion of the catheter until the shaft portion extends beyond the stylet point and into the vein. The stylet is then withdrawn and intravenous connection made to the cathode adapter. This requires the use of both hands as the technician must hold the released catheter in place with one hand while discarding the stylet with the other hand and after discarding the stylet, the technician picks up the dressing to cover the point of incision. In addition to the hazards and difficulties involved in this operation, the use of the technician's hand to hold the catheter increases the chances of bacterial contamination, even if the technician is wearing surgical gloves.

Despite several attempts in the past to overcome these problems, only limited success was achieved. In U.S. Pat. No. 4,713,057 of Huttner et al., for example, a catheter apparatus is shown having a pair of handles with forwardly projecting struts. The releasing handle has a first strut secured to the hub body of the catheter and a forward strut which is wedged between the catheter adapter and a circumferential flange fitted around the adapter for this purpose. By applying pressure on the handle, the forward strut is pushed against the flange thereby directing the catheter axially forward of the stylet. While this satisfies the requirement for the single handed release of the catheter forward of the needle point, the catheter adapter must have a circumferential flange which adds to the bulk of the adapter. When the intravenous line is ultimately connected, clothing or bedclothes could rub against this flange causing discomfort to the patient.

Another attempt at single hand forward action of a catheter device is found in U.S. Pat. No. 4,191,970 of Hession. In this reference, the catheter adaptor or hub includes a drive plate which abuts against a firing arm mounted on the catheter body portion. By finger action on the striking arm, the drive plate propels the accompanying catheter into the vein. In addition to the dangers involved in forcefully thrusting a catheter into the vein where it might completely puncture the vein, such a catheter would then be left with the cumbersome drive plate on its hub or adapter once the intravenous line is connected.

In U.S. Pat. No. 4,191,188 of Keller, another attempt was made to release a catheter from the end of the stylet by means of single finger action. This device has a separate catheter mount which is placed over the stylet hub or adapter before use. After the stylet is inserted into the patient's vein, the catheter and catheter hub can be moved forward by grasping the stylet hub with two or three fingers while pushing a digit engaging means with the thumb until the catheter advance forward. However, once the intravenous line is connected the digit engaging means proves to be bulky and uncomfortable. It can be twisted or snapped off, but this requires another forceful action at a time when the intravenous line is connected.

The applicant has devised a catheter insertion apparatus having a simple and relatively inexpensive releasing means which can be integral with the catheter chamber guard. It can therefore be constructed as a single unit thereby reducing manufacturing costs. Furthermore, since forward movement of the catheter by means of the applicant's threader involves even and controlled forward movement, the danger of forceful forward thrusting of the catheter in the vein is eliminated. As will be described below, the use of the applicant's catheter reduces the changes of bacterial infection as the technician's hand does not have to come in contact with the catheter adapter.

It is therefore an object of one aspect of this invention to provide a catheter insertion apparatus which reduces the chances of infection during the insertion and intravenous connection.

It is an object of another aspect of this invention to provide a catheter insertion apparatus which permits even and controlled forward projection over the stylet point when inside the vein of a patient.

It is an object of yet another aspect of the invention to provide a catheter insertion apparatus wherein stylet insertion and forward movement of the catheter can be carried out as a single handed operation.

These and other objects are achieved by means of a catheter insertion apparatus comprising:

a) a body member having a forwardly projecting hub and a central opening therein defining a backflow chamber;

b) a stylet mounted forwardly on said body having a central opening therethrough with its forward end extending to a point for insertion into a patient and rearward end connected through said hub in communication with said backflow chamber;

c) a catheter member having an adapter portion for releasable mounting over said hub and a shaft portion for extending axially from said adaptor portion over said stylet and terminating short of said stylet point when the hub portion is so mounted;

d) a chamber guard releasably mounted on said body member rearwardly of said backflow chamber for closing the rear end thereof, said chamber guard including a single threader member integral therewith and in a forwardly extending loop, the leading end of which further extends along an outer surface of said body member and said hub to abut the adapter portion of said catheter member whereby downward finger pressure on said loop causes the leading end to advance and displace the catheter member along a line of axial displacement beyond said stylet point.

In the Drawings:

FIG. 1 is a perspective view of the apparatus with the catheter shown in extended relationship thereto;

FIG. 2 is a cross-sectional side elevation of the apparatus of FIG. 1 with the catheter mounted in position;

Figure 4:
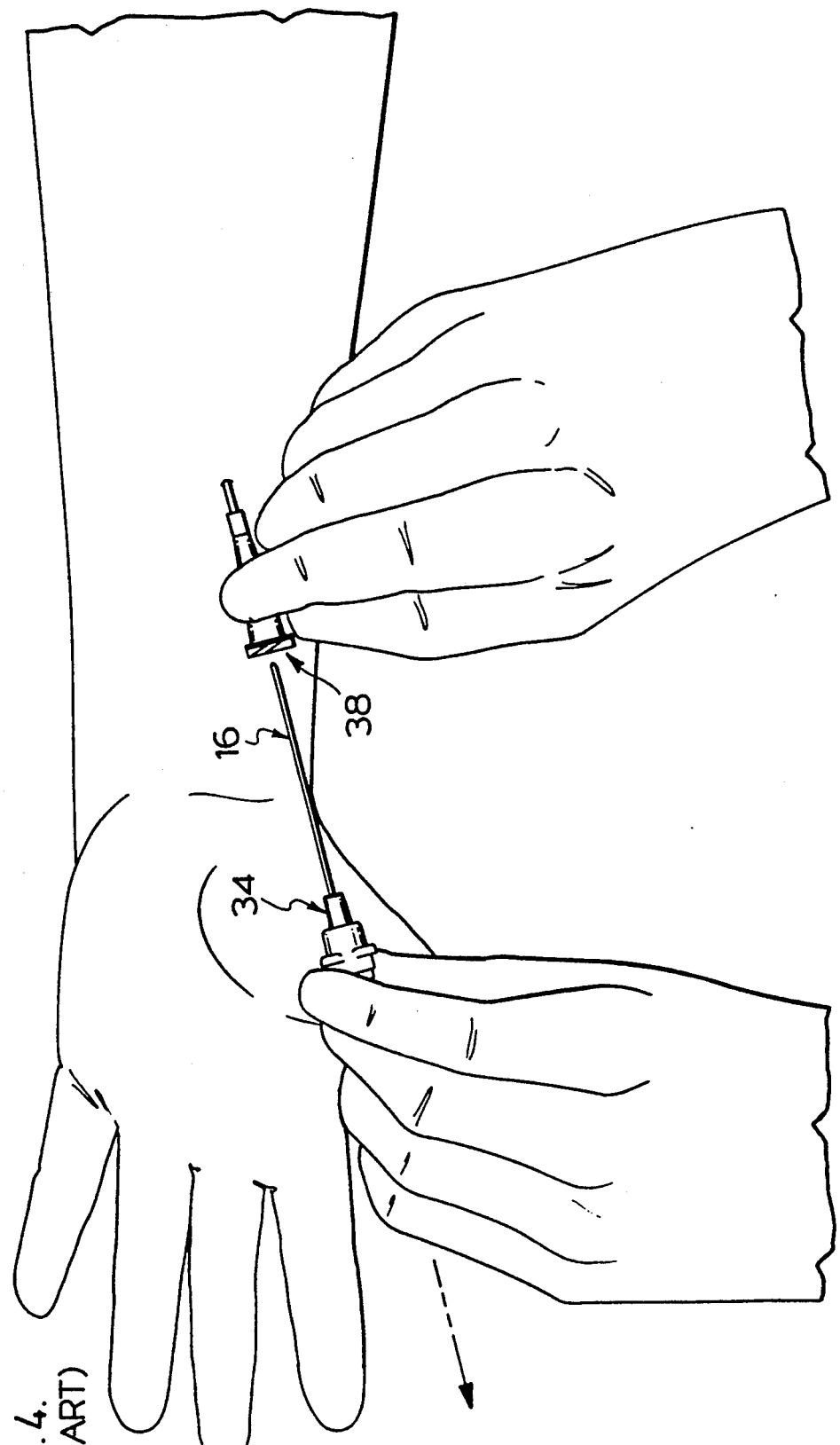
FIG. 4 is an illustration of a method for the subcutaneous insertion of a catheter into a patient using a conventional catheter device.

The catheter invention apparatus and accompanying catheter is indicated generally at 10 in FIGS. 1 and 2 and includes a body member 12 having a forwardly projecting hub 14 and a hollow stylet 16 projecting forwardly therefrom. Stylet 16 has a bevelled pointed front end 18. As can be seen particularly in FIG. 2, stylet 16 is secured through hub 14 to communicate with a backflow chamber 20 in body member 12. Backflow chamber 20 is closed off by a removable chamber guard 22. Chamber guard 22 is fitted over the rearward end of body 12 by inserting the rime of the substantially cylindrical rearward portion of body 12 into the grooves defined between the centrally projecting end wall 24 of chamber guard 22 and its accompanying out rim 26.

A catheter member 28 is shown spaced from the catheter insertion apparatus in FIG. 1 and shown mounted in position in FIG. 2. Catheter member 28 includes an adapter portion 30 at its rearward end and a shaft portion 32 at its front end. When the catheter adapter is positioned over mount 34 of hub 14 as shown in FIG. 2, the shaft portion 32 is axially extended around stylet 16 but extends somewhat short of the pointed end 18.

Chamber guard 22 includes a threader member 36 which is integral at its rearward end with the wall of the chamber guard. This threader member is made of a resilient material, usually plastic, and of the same material as the chamber guard itself. Threader member 36 is formed into a loop which extends forwardly and downwardly to body member 12, where its axially leading end continues along the body member until it contacts the lip 38 of catheter adapter 30 the catheter mounted in position.

Body member 12 includes a groove 40 of such a width as to accommodate the leading end of threader member 36 and provide an axial passage for moving the leading end forward when downward pressure is exerted on the loop. This groove extends along the body and through the centre of hilt flange 42. When the threader member 36 is urged forward, its leading edge will be centrally maintained to pass over hub 14 and abut against lip 38 of catheter member 28. Downward finger pressure on loop portion of threader member 36 will cause its leading end to push against lip 38 and urge the catheter member 28 forward in a manner to be particularly described with reference to FIG. 3.

As an optional feature, the apparatus can include one or more retaining bands 44 wrapped around body member 12 at its forward end but behind hilt flange 42, in order to insure that the leading end of threader member 36 is maintained within groove 40.

Figure 3:
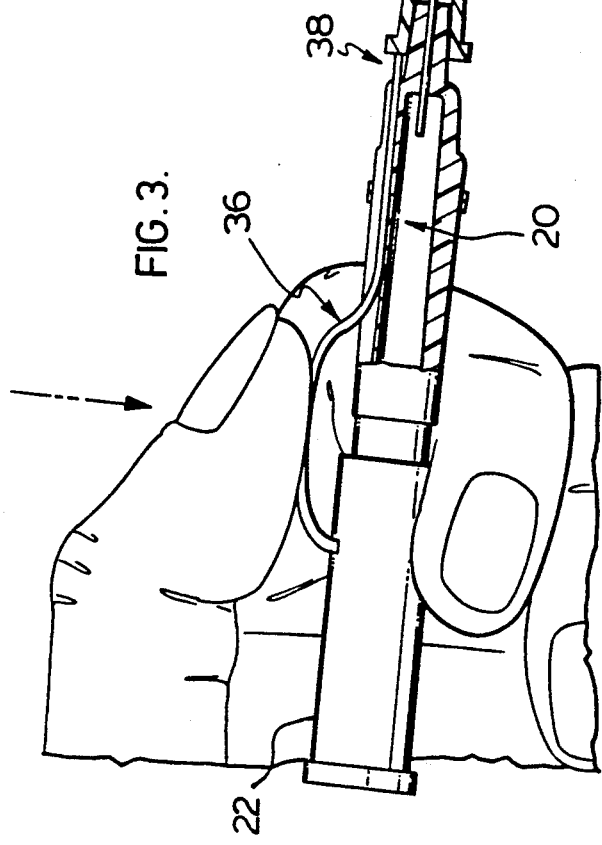
FIG. 3 is an illustration of a method for handling the apparatus of the present invention during intravenous administering of a catheter to a patient.

The action of directing the catheter forward by applying downward pressure on the threaded member is more particularly illustrated in FIG. 3. In this figures, the pointed edge 18 of stylet 16 is shown having pierced through the epidermal surface 46 of a patient and into a vein 48. Downward thumb pressure is applied to the loop of threader member 36 by the medical technician with the same hand that is holding the insertion apparatus. This downward pressure directs the leading end of threader member 36 forward until it pushes against lip 38 of catheter member adapter 30. The catheter member is then directed axially forward until its shaft portion 32 extends beyond the pointed end 18 of stylet 16. Forward direction in this manner allows the medical technician to control the insertion of the stylet so that it only reaches into the vein. This point is indicated by a "flashback" of blood into backflow chamber 20.

The technician then discontinues further forward movement of the stylet and applies thumb pressure on threader member 36 to urge the catheter forward beyond the stylet point and further into the vein. By directing the catheter shaft 32 beyond the stylet point, the technician reduces the changes of ripping through the vein yet insures that the catheter shaft is well placed.

In addition to reducing the chances of trauma resulting from the accidental ripping of a vein, the method of inserting the catheter is simplified and the medical technician has more control over the patient. It also reduces the chances of infection since the catheter itself does not have to be handled by the technician.

FIG. 4 illustrates the usual method for inserting a catheter with the conventional apparatus. In the embodiment illustrated, the technician has already inserted the stylet through the patient's skin and located a vein. With the conventional catheter insertion apparatus, the technician must continue to urge the stylet into the vein to insure proper positioning of the catheter. When the catheter member is fully inserted then the technician holds the catheter hub with the right hand as shown in the figure and withdraws the apparatus and stylet with the left. There are two important drawbacks to this method. If the patient is under stress and unable to remain still, the technician does not have control of the patient.

Another serious setback is that the technician must grasp the hub of the sterile catheter thereby raising the possibility of bacterial contamination in the incision even if the technician is wearing surgical gloves. The apparatus must then be set aside and the required intravenous line connected to the catheter hub and a dressing applied across the incision.

Figure 5:
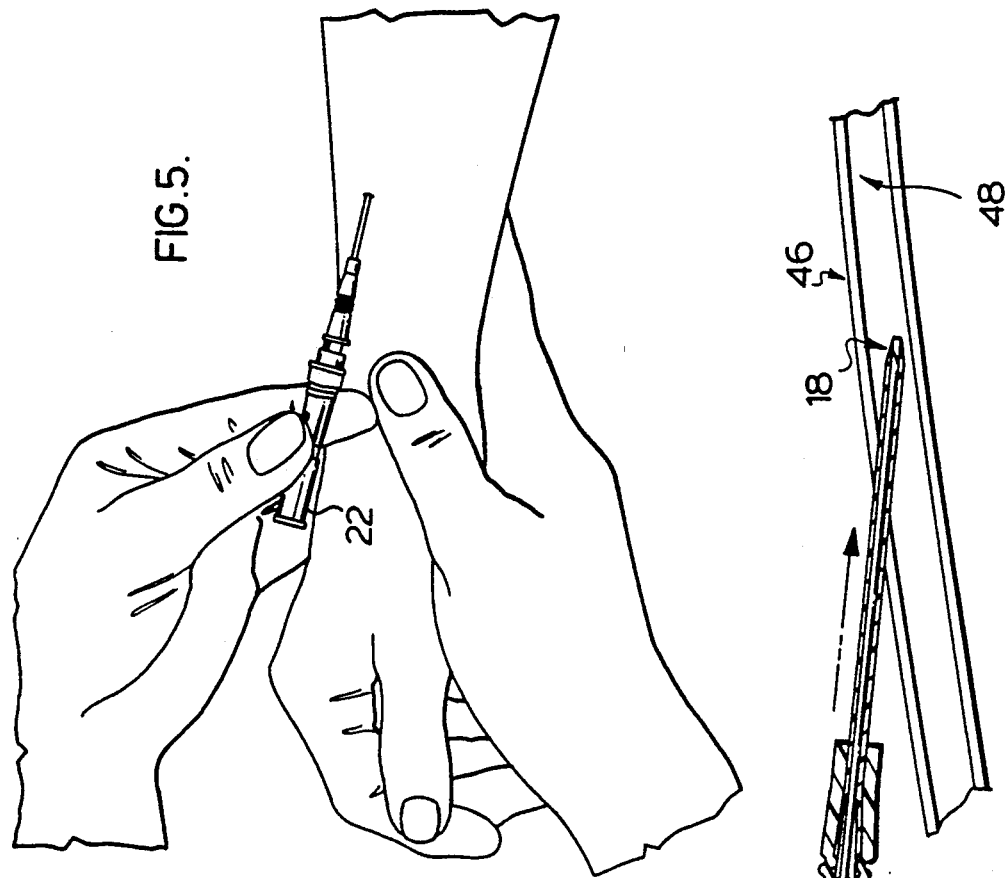
FIG. 5 is an illustration of a method for the subcutaneous insertion of a catheter into a patient using the apparatus of the present invention.

FIG. 5 illustrates a simple method for inserting the catheter using the apparatus of the present invention. In the illustration of FIG. 5, the medical technician holds the patient arm with this right hand while inserting the stylet through the epidermal surface to locate a vein. When the vein is thus located, a "flash back" of blood enters the backflow chamber and the technician applies thumb pressure on the threader member to urge the catheter forward so that the catheter shaft is fully inserted into the vein. A dressing is applied to the incision and the apparatus and stylet are then withdrawn by the left hand and discarded. An intravenous line is then connected to the catheter hub.

The improvement of the applicant's apparatus can be made in a conventional catheter insertion apparatus by undergoing a few economical modifications. For example, the conventional catheter chamber guard, which is manufactures separate from the catheter body, is usually made of a resilient ethylene polymer material. The threaded member can be formed as an integral part thereof.

A longitudinal groove can be made along one side of the apparatus body during its construction. The body is usually made of a rigid plastic material. One or more retaining bands can be wrapped around the body as an optional feature. No modification need otherwise be made in the conventional type of catheter member. The catheter adaptor and lip portion are small enough to avoid creating a bulky inconvenience when the intravenous line is connected.

It can be appreciated that minor modifications can be made in the applicant's apparatus without departing from the scope of the invention as described and illustrated in the specification or as recited in the accompanying claims.

I claim:

1. A catheter insertion apparatus for the subcutaneous insertion of a catheter into a patient, comprising;
   a) a body member having a forwardly projecting hub and a central opening therein defining a backflow chamber;
   b) a stylet mounted forwardly on said body having a central opening therethrough with the forward end extending to a point for insertion into a patient and a rearward end connected through said hub in communication with said backflow chamber;
   c) a catheter member having an adaptor portion for releasable mounting over said hub and a shaft portion for extending axially from said adaptor portion over said stylet and terminating short of said stylet point when the hub portion is so mounted;
   d) a chamber guard releasably mounted on said body member rearwardly of said backflow chamber for closing the rear end thereof, said chamber guard including a single threader member integral therewith and in a forwardly extending loop, the leading end of which further extends along an outer surface of said body member and said hub to abut the adaptor portion of said catheter member whereby downward finger pressure on said loop causes the leading end to advance and displace the catheter member along a line of axial displacement beyond said stylet point said outer surface including a grooved surface thereon for directing said leading end along said line of axial displacement.

2. An apparatus as claimed in claim 1 which includes at least one band member around said body and said threader member for retaining said threader member within said grooved surface.

3. An apparatus as claimed in claim 1 where said outer surface and said hub includes a grooved surface thereon for directing said leading end along the line of axial displacement.

4. An apparatus as claimed in claim 3 which includes a further band member around said hub and said threader member for retaining said threader member within said grooved surface.

* * * * *